United States Patent [19]

Miyazaki

[11] 4,389,513
[45] Jun. 21, 1983

[54] HIGHLY ABSORBENT RESIN
[75] Inventor: Hirotoshi Miyazaki, Ibaraki, Japan
[73] Assignee: Kuraray Company, Limited, Kurashiki, Japan
[21] Appl. No.: 309,773
[22] Filed: Oct. 8, 1981
[30] Foreign Application Priority Data Oct. 22, 1980 [JP] Japan .................. 55/148639

[51] Int. Cl.$^3$ .............................................. C08F 8/32
[52] U.S. Cl. .................................. 525/186; 525/381; 525/382
[58] Field of Search ............................... 525/186, 381
[56] References Cited
U.S. PATENT DOCUMENTS

| 3,506,625 | 4/1970 | Patinkin | 525/381 |
| 3,678,016 | 7/1972 | Zimmerman et al. | 525/381 |
| 3,786,113 | 1/1974 | Vassileff | 525/186 |
| 4,085,060 | 4/1978 | Vassileff | 525/186 |
| 4,241,682 | 12/1980 | Konstandt | 525/186 |

Primary Examiner—Paul Lieberman
Assistant Examiner—Robert E. L. Sellers
Attorney, Agent, or Firm—Oblon, Fisher, Spivak, McClelland & Maier

[57] ABSTRACT

A highly absorbent resin which is essentially a polyamine-crosslinked, partial neutralization product obtained by reaction of an alkali metal hydroxide with a carboxyl-containing polymer selected from the froup consisting of alpha-olefin-maleic anhydride copolymers, vinyl compound-maleic anhydride copolymers, polyacrylic acid, polymethacrylic acid, and mixtures thereof, the degree of neutralization of the said neutralization product being 0.4 to 0.8 equivalent of total carboxyl groups of the said carboxyl-containing polymer, the amount of polyamine as a crosslinking agent being not more than 2 parts by weight per 100 parts by weight of the neutralization product on the uncrosslinked basis, the resin being capable of absorbing at least 20 times its own weight of distilled water. The resin has good resistance to heat and good durability in the hydrous condition.

15 Claims, No Drawings

HIGHLY ABSORBENT RESIN

BACKGROUND OF THE INVENTION

1. Field of the Art

This invention relates to a highly absorbent resin which is essentially a polyamine-crosslinked, partial neutralization product obtained by reaction of an alkali metal hydroxide with a carboxyl-containing polymer selected from the group consisting of alpha-olefin-maleic anhydride copolymers, vinyl compound-maleic anhydride copolymers, polyacrylic acid, polymethacrylic acid, and mixtures thereof, said resin being capable of absorbing at least 20 times its own weight of distilled water and having good durability and good heat resistance in the hydrous condition.

2. Description of the Prior Art

Apart from those materials capable of absorbing at most 10 and odd times their own weight of water, including synthetic resins useful as ion exchangers or ion adsorbers (see, for example, Japanese Patent Application Kokai No. 50-78,583), fibrous materials (e.g. absorbent cotton, wool), pulp, and porous particulate or granular inorganic materials (e.g. porous active carbon, vermiculite), hydrophilic polymeric materials capable of absorbing at least 20 times their own weight of distilled water have recently become subjects of increasing interest because of their high water-absorbing capacity. In particular, those polymer materials that can, on contact with water, absorb a very large amount of water rapidly in a short time are expected to be useful in making sanitary napkins or tampons, diapers, disposable towels for kitchen use, and soil conditioners, for instance. As such polymer materials, there have recently been proposed several materials derived from natural or synthetic high molecular substances, such as crosslinked polyoxyethylene oxide, crosslinked polyvinyl alcohol, hydrolyzate of starch- or cellulose-polyacrylonitrile graft copolymer and crosslinked carboxymethylcellulose. These highly absorbent resins are now used not only in disposable hygienic and household articles, such as sanitary napkins, tampons, diapers and kitchen articles, but also in the industrial field, for example as water leak stoppers and dehydrating agents, which make good use of water swellability of the resins, and in the field of civil engineering and construction industry, for example as soil conditioners and dew formation inhibitors. Accordingly, the requirements to be met by the highly absorbent resin are that the physical properties of the resins in the hydrous condition, that is the physical properties of the hydrous gels, do not alter upon standing for a long period of time in the hydrous condition, that the resins can endure hot water for a long period, that the resins have good heat resistance, and that the resins are resistant to acids and alkalis. However, it is no exaggeration to say that none of the above-mentioned commercially available resins and the resins under development has all of these physical properties including durability. Thus, for instance, the highly absorbent resins derived from starch or carboxymethylcellulose, when left standing in the hydrous condition, easily undergo biodegradation or decay and as a result a sufficient degree of durability cannot be expected in them. The highly absorbent resins derived from synthetic high molecular substances, such as those consisting of copolymers of a hydrophilic vinyl monomer (e.g. acrylic acid, methacrylic acid) and diacrylate or dimethacrylate of a polyol (e.g. ethylene glycol) (Japanese Patent Application Kokai No. 55-99,986) and those consisting of urea resin- or melamine resin-crosslinked alpha-olefin-maleic anhydride copolymers (Japanese Patent Application Kokai No. 54-94,525), mostly contain ester or amide bond-containing crosslinks, and consequently are susceptible to hydrolysis in the hydrous condition or in the hot hydrous condition. The hydrolysis leads to breakage of the crosslinks, and, in most cases, the initial properties of hydrous gels cannot be retained for a long period. The highly absorbent resins disclosed by Japanese Patent Application Kokai No. 53-25,666 or U.S. Pat. No. 4,155,957, which are prepared by dissolving a lower olefin-maleic anhydride copolymer in ammonia water, adding thereto a compound containing at least two hydroxyl groups (e.g. ethylene glycol, propylene glycol, glycerol), a compound containing at least two amino groups (e.g. ethylenediamine, propylenediamine), a compound containing at least two epoxy groups (e.g. diglycidyl ether) or the like (e.g. glycidyl alcohol), together with an aqueous ethylene-vinyl acetate copolymer emulsion, and allowing the crosslinking reaction to proceed, lose their water-absorbing capacity almost completely on exposure to elevated temperatures.

SUMMARY OF THE INVENTION

A primary object of the present invention is to provide highly absorbent resins capable of absorbing 20 to 800 times their own weight of water (distilled water) and at the same time having good durability. Another object is to provide a method of producing highly absorbent resins having an absorbency as desired in a very simple manner.

The term "highly absorbent resins" as used herein means resins giving absorbency values (g/g) of at least 20, preferably 50 or more, and consequently sharply distinguishable from the previously mentioned synthetic resins, fibrous materials, pulp, and porous materials such as porous active carbon and porous inorganic particles, which give absorbency values of at most 10 and odd. Absorbent materials giving absorbency values of less than 20 can absorb water only a slow rates but cannot be used in cases where a great water-absorbing capacity is required, for example, in the cases of sanitary articles, diapers, disposable kitchen towels, water leak stoppers and soil conditioners. If soluble in water, the absorbent resins cannot be adequate for the above-mentioned applications. Therefore, the resins should have a degree of crosslinking such that they swell without dissolving in water. In most cases, the maximum absorbency is about 800 g/g, which is quite sufficient. Preperably, resins having an absorbency of 50-500 are generally used. The "absorbency" is herein defined, unless otherwise stated, as parts by weight of distilled water absorbed by the absorbent resin per part by weight of the resin before swelling, hence may be expressed on the g/g basis.

By "good durability" is meant that the highly absorbent resin does not degenerate in the hydrous condition, i.e. in the form of hydrous gel, during a prolonged period of storage, can endure hot water for a long period, and can resist acids and alkalis. Absorbent resins having good durability alone can adequately be used as water leak stoppers, dehydrating agents, etc. in the field of industry and as soil conditioners, dew formation inhibitors, etc. in the field of civil engineering and construction.

"Producing highly absorbent resins having an absorbency as desired in a very simple manner" means that the crosslinking reaction can be conducted very easily and safely using water, which, in most cases, requires little consideration of possible environmental pollution thereby or recovery thereof, as the solvent and that, since the absorbency of the highly absorbent resin correlates in a very simple manner with the amount of crosslinking agent used, highly absorbent resins with an absorbency as desired can be obtained easily, hence the industrial production process can be managed very easily.

In accordance with the present invention, the above objects are realized by providing highly absorbent resins which essentially are polyamine-crosslinked, partial neutralization products obtained by reaction of an alkali metal hydroxide with a carboxyl-containing polymer selected from the group consisting of alpha-olefin-maleic anhydride copolymers, vinyl compound-maleic anhydride copolymers, polyacrylic acid, polymethacrylic acid, and mixtures thereof, the degree of neutralization of the said neutralization products being 0.4 to 0.8 equivalent of total carboxyl groups of the said carboxyl-containing polymer, the amount of polyamine as a crosslinking agent being not more than 2 parts by weight per 100 parts by weight of the neutralization products on the uncrosslinked basis, said resins being capable of absorbing at least 20 times their own weight of distilled water.

DETAILED DESCRIPTION OF THE INVENTION

The neutralization product of carboxyl-containing polymer to be used in accordance with the invention is an alkali metal neutralization product obtainable by reacting an alkali metal hydroxide with a polymer containing carboxyl groups or functional groups convertible to carboxyl groups in the presence of an alkali hydroxide, such as a maleic anhydride copolymer comprising an alpha-olefin or a vinyl compound and maleic anhydride (inclusive of maleic acid, maleic acid ester or other maleic acid derivative), or an acrylic acid polymer such as polyacrylic or polymerthacrylic acid. When vinyl polymers containing other functional groups are used, the resulting absorbent resins, as mentioned above, will no longer have good durability. When acidic ammonium or amine salts of a carboxyl-containing polymer are used, the use of the polyamine-crosslinked products will be subject to severe restrictions, because they give off odor due to ammonia or amine liberation therefrom, are poor in resistance to heat and hot water, lose their performance characteristics as high absorbent resins upon heating or upon attack of hot water, show a rapid decrease in the absorbency as a result of being affected by salts or ions if these are present in the water to be absorbed, and have other disadvantages. To the contrary, the highly absorbent resins obtainable by crosslinking alkali metal neutralization products of the above-mentioned specific carboxyl-containing polymers with polyamines are free from the drawbacks which are inherent to the highly absorbent resins derived from other polymers than the above-mentioned carboxyl-containing polymers or from ammonium or amine salts of carboxyl-containing polymers, and at the same time are very excellent in physical and chemical stability, hence in durability, because ion complexes between the carboxyl group and polyamine are involved in the crosslinks. Concretely, hydrous gels prepared by adding water to the highly absorbent resins of the invention neither reveal any signs of breakdown in the hydrous gel structure nor significant change in the absorbency after storage in hermetically sealed containers at room temperature for more than a year, or after heating at 70° C. for several months, or after boiling at 100° C. for several days. They are resistant to biodegradation by decaying microbes. The hydrous gels are not distintegrated even when heated in aqueous solutions of acids or alkalis. In this manner, the resins have semipermanent durability even in the hydrous condition. It goes without saying that the resins are excellent in durability in the dry condition.

The maleic anhydride copolymers prepared from an alpha-olefin or vinyl compound and maleic anhydride, which are useful in preparing alkali metal neutralization products of carboxyl-containing polymers in accordance with the invention are described hereinafter in more detail.

The term "alpha-olefin" as used herein includes within the meaning thereof straight or branched unsaturated aliphatic hydrocarbons containing 2–12, preferably 2–8, carbon atoms, such as ethylene, propylene, butene-1, butene-2, isobutylene, n-pentene, isoprene, 2-methyl-1-butene, n-hexene, 2-methyl-1-pentene, 3-methyl-1-pentene, 4-methyl-1-pentene, 2-ethyl-1-butene, diisobutylene, 1,3-butadiene, 1,3-pentadiene, 1,3-hexadiene, 1,3-octadiene and 2-methyl-4,4-dimethyl-1-pentene. As a source for said isobutylene, the so-called return or spent BB fraction or stream may also be used.

The term "vinyl compound" as used herein includes within the meaning thereof unsaturated compounds (except for the above alpha-olefin) copolymerizable with maleic anhydride, such as styrene, vinyl chloride, vinyl acetate, vinyl propionate, acrylonitrile, methyl vinyl ether and an acrylic acid ester.

These monomers may be used either alone or in combination of two or more species. Among them, preferred are such alpha-olefins as ethylene and isobutylene, styrene and methyl vinyl ether. In particular, alpha-olefins, especially isobutylene, are the most adequate monomers for the purposes of the present invention.

The ratio of the alpha-olefin or vinyl compound to maleic anhydride in such a maleic anhydride copolymer is optional only if the reaction product (alkali metal neutralization product) from the resulting copolymer and an alkali metal hydroxide would be soluble in water. In the case of the copolymers of maleic anhydride with ethylene, isobutylene styrene or methyl vinyl ether which are preferably used in the practice of the present invention, ethylene, isobutylene, styrene or methyl vinyl ether is used in an amount of about 1–3 moles, in most cases about 1 mole, per mole of maleic anhydride.

These maleic anhydride copolymers may be used either alone or in combination of two or more species. It is desired that they have a molecular weight such that the intrinsic viscosity $[\eta]$ thereof as measured in dimethylformamide at 30° C. is within the range of 0.1 to 8 (dl/g), preferably 0.2 to 5 dl/g). When the intrinsic viscosity is smaller than 0.1, the rate of crosslinking becomes very slow and resins with high absorbency can hardly be produced. On the other hand, when the intrinsic viscosity is higher than 8, the viscosity of the solution prepared from the resin becomes so high that workability or operability problems tend to arise in the production of highly absorbent resins.

More detailed explanation is now given to the (meth)acrylic acid polymers. By "polyacrylic acid" or "polymethacrylic acid" is meant a polymer obtained by polymerizing acrylic acid or methacrylic acid in a solvent (e.g. water, organic solvent). "Poly(meth)acrylic acid" may be a hydrolyzate of poly(meth)acrylic acid ester, poly(meth)acrylonitrile, poly(meth)acrylamide or the like. The poly(meth)acrylic acid may contain a small amount of a vinyl compound copolymerizable therewith.

The molecular weight of the (meth)acrylic acid polymer is desirably such that the intrinsic viscosity $[\eta]$ as measured in an electrolyte-containing aqueous solution at 30° C. is within the range of 0.1 to 10 (dl/g), preferably 0.5 to 8 (dl/g).

Among these carboxyl-containing polymers, isobutylene-maleic anhydride copolymer is the most preferred one, because the viscosity of a solution thereof is relatively low, which renders it possible to carry out the reaction at a relatively high concentration, and because it gives highly absorbent resins with very good durability.

These carboxyl-containing polymers are converted to alkali metal neutralization products by reacting with an alkali metal hydroxide. This reaction is effected, for example, by adding a carboxyl-containing polymer to an aqueous solution of an alkali metal hydroxide.

The alkali metal hydroxide to be used herein includes among others sodium hydroxide, potassium hydroxide and lithium hydroxide. It reacts with the carboxylic acid or acid anhydride functions of the carboxyl-containing polymer to render the same water soluble or at least hydrophilic if not completely water soluble. While the use of an alkali metal hydroxide is essential, two or more alkali metal hydroxides may be used in combination. A small amount of ammonia may be used to promote dissolution of the said carboxyl-containing polymer in water or accelerate the crosslinking reaction between the carboxyl-containing polymer and the polyamine, as mentioned after. On the contrary, the use of ammonia or an amine alone will result not only in formation of highly absorbent resins having an odor of ammonia or amine but also in significant decrease in durability thereof, hence cannot achieve the expected results.

For achievement of the objects of the invention as mentioned above, it is essential that the degree of neutralization of the carboxyl-containing polymer with an alkali metal hydroxide is within the range of 0.4 to 0.8, preferably 0.5 to 0.8. When the degree of neutralization of the carboxyl-containing polymer is outside said range, the resulting resins, though highly capable of absorbing water, are very low in durability, especially in resistance to hot water, in the hydrous condition. The term "degree of neutralization" is used herein, for the case of maleic anhydride copolymers, for instance, to report the extent to which the carboxyl groups contained in the polymer are neutralized with the alkali metal hydroxide on the basis such that the degree of neutralization is equal to 1 when two moles of alkali metal hydroxide is reacted with one mole of maleic anhydride, and for the (meth)acrylic acid polymers, on the basis such that the degree of neutralization is equal to 1 when one mole of alkali metal hydroxide is reacted with one mole of the carboxylic acid.

In accordance with the present invention, polyamines are specifically used as the crosslinking agents. With other agents capable of crosslinking the carboxyl-containing polymers, such as epoxy compounds, polyhydric alcohols and isocyanates, among others, the water-absorbing capacity of the highly absorbent resin products fluctuates from lot to lot, or the resin manufacture requires very high temperatures or special solvents, so that the control of the crosslinking reaction becomes very difficult, or in some cases where some crosslinking agents are used, the highly absorbent resins having good durability, which are the subjects of the present invention, cannot be produced. On the contrary, the use of polyamines makes it very easy and simple to carry out the reaction on the industrial scale using water as the solvent. Moreover, when polyamines are used, the absorbency of the resulting highly absorbent resins is substantially decided by an exponential function of the amount of the crosslinking agent (polyamine) used. Therefore, preliminary determination of two or three absorbency values in correlation with the corresponding known amounts of polyamine will render it very easy to produce highly absorbent resins with desired degree of absorbency thereafter. Such characteristic features can specifically be noted only with polyamines. Moreover, the highly absorbent resins produced by crosslinking with polyamines are, as mentioned above, very excellent in durability.

Such polyamines specifically useful as crosslinking agents are water-soluble polyamines having a general formula shown by $H-(NH-CH_2-CH_2-)_nNH_2$, wherein n is an integer of 1 to 110, such as ethylenediamine, diethylenetriamine, triethylenetetramine, tetraethylenepentamine, pentaethylenehexamine, and straight or branched polyethyleneimine. It is preferred, from the viewpoint of the performance of the highly absorbent resins, that the polyamines have a molecular weight of 60-5,000.

The amount of the polyamine to be used per 100 parts by weight of the alkali metal neutralization product carboxyl-containing polymer is generally within the range of more than 0.05 part by weight to less than 2 parts by weight, depending on the kind of said alkali metal neutralization product and/or the polyamine. When the amount is significantly smaller than 0.05 part by weight, not only the highly absorbent resin product, when swollen, presents only extremely low gel strength, that is poor durability, but also such problems as mutual adhesion of the highly absorbent resin particles or partial dissolution of the resin in water are encountered, although the absorbency of the highly absorbent resin is favorably increased. On the contrary, when the amount significantly exceeds the above range, the crosslink density of the resulting highly absorbent resin becomes so high that the absorbency in return becomes decreased, and as a result highly absorbent resins which are subjects of the present invention cannot be obtained any longer. From this viewpoint, the amount of polyamine is preferably within the range of 0.14 to 1.7 parts by weight. This range is preferably employed in producing highly absorbent resins by crosslinking sodium neutralization products of isobutylene-maleic anhydride copolymers with polyethyleneimine, since polyethyleneimine used in amounts within this range gives highly absorbent resins with absorbency values of 20-800 g/g. Based on the relation between the amount of polyamine and the absorbency of the resulting highly absorbent resin, the amount of polyethyleneimine to be used for obtaining generally preferred high absorbent resins with absorbency values of 50–500 is calculated at 0.2 to 0.9 part by weight. This range is thus preferred for polyethyleneimine.

A typical method of crosslinking an alkali metal neutralization product of a carboxyl-containing polymer with a polyamine comprises dissolving the alkali metal neutralization product in a solvent such as water or an alcohol, preferably water, adding to the solution an adequate amount of the polyamine to bring about a desired degree of absorbency in the final highly absorbent resin product, and stirring the mixture until a homogeneous solution is formed, followed by drying and heat treatment. As the solution of the alkali metal neutralization product, there may also be used the solution formed when the alkali metal hydroxide is reacted with the carboxyl-containing polymer, as it is, without any inconvenience. Fairly severe conditions are required for the above-mentioned crosslinking reaction. Generally, it is required, after removing the reaction solvent such as water or an alcohol, to carry out a certain heat treatment so as to bring the crosslinking reaction to completion. When, for example, the temperature is raised in the step of removing the solvent used in the crosslinking reaction by drying or evaporation, the drying and crosslinking reaction can be carried out in one and the same step.

The thus-produced highly absorbent resins present those characteristic features that the conventional highly absorbent resins never have presented. Thus, they show high absorbency and are capable of absorbing 20–800 times their own weight of distilled water at high rates of water absorption. They are also excellent in absorption capacity to salt solutions, urine and blood. They are durable not only in the dry condition but also in the hydrous condition and can retain their performance characteristics constantly over a prolonged period of time.

The form of the thus-produced highly absorbent resins is not critical. The resins may be crushed or comminuted in a conventional manner to form powders thereof or may have the form of films, without causing any inconvenience. Furthermore, paper, woven or nonwoven fabrics, or the like may be coated with the solution prior to effecting polyamine crosslinking, followed by drying and crosslinking. In this case, the products are absorbent articles in the form of paper, woven or nonwoven fabrics or the like containing the highly absorbent resins.

To the highly absorbent resins of the present invention, there may be added fillers, pigments, colorants, ultraviolet absorbers, antioxidants, antifungal agents, bactericides, insecticides, herbicides, fertilizers, perfumery, deodorants, etc.

The highly absorbent resins of the present invention are useful in a variety of applications. Thus, for example, when used in making disposable diapers, sanitary articles, gauze, disposable towels and the like, they give articles excellent in liquid absorbing capacity. When mixed with soil, they increase the water-holding capacity of the soil. When they are used in making materials for interior decoration, the materials have dew formation inhibiting properties. When they are impregnated with pesticides, fertilizers and perfumery substances, for instance, leaching or washing away of these substances can be inhibited. Furthermore, addition of the highly absorbent resins to aqueous mixtures such as emulsions and latexes followed by filtration may achieve concentration of these aqueous mixtures.

By making use of their excellent durability, the highly absorbent resins of the present invention can also be used favorably in such industrial applications as sealants, packings and water leak stoppers, for instance.

The present invention is more fully illustrated by, but never limited to, the following examples.

EXAMPLE 1

A mixture of 100 weight parts of isobutylene-maleic anhydride copolymer (the intrinsic viscosity $[\eta]$ as measured in dimethylformamide at 30° C. being 1.01; the molar ratio of isobutylene to maleic anhydride in the copolymer being 1:1; ISOBAM ®-10, product of Kuraray Isoprene Chemical Co., Ltd.), 26 weight parts of sodium hydroxide and 374 weight parts of water was stirred with heating. A homogeneous aqueous solution of acidic sodium salt of isobutylene-maleic anhydride copolymer was thus prepared. The degree of neutralization of the neutralization product was 0.5. Then, 0.5 weight part of polyethyleneimine having a molecular weight of 1,200 was added to 500 weight parts of the above aqueous solution, and the mixture, after adequate stirring, was formed into a film by pouring into a square Teflon vat (70×70 cm). The film was dried in an air oven maintained at 120° C. and further heat-treated at 160° C. for 3 hours. Thereafter, the film was crushed to form a highly absorbent 20-mesh resin powder.

The highly absorbent resin powder thus prepared was insoluble in water, swelled rapidly in water and absorbed 280 g/g of distilled water. The swollen resin was transparent, and showed a sufficient gel strength, without mutual adhesion of the resin particles. The resin powder absorbed 85 g/g of 0.5% sodium chloride solution and 60 g/g of Ringer solution. Durability tests were conducted for the highly absorbent resin by the following methods:

(1) Durability test A

To 1 g of the highly absorbent resin is added 200 g of water, the container is hermetically sealed so as to prevent evaporation of water, the mixture is stored at room temperature (15°–25° C.) for a year, and the condition of the hydrous gel is observed. When the condition of the hydrous gel remains unchanged as compared with the initial one, the result is reported by the mark O; when partial dissolution of the hydrous gel is observed, by the mark Δ; and when dissolution is complete and the state of hydrous gel is not noted any longer, by the mark X.

(2) Durability test B

To 1 g of the highly absorbent resin is added 200 g of water, the container is sealed hermetically so as to prevent evaporation of water, the mixture is heated at 70° C. for 30 days, and the condition of the hydrous gel is observed. The result is reported in the manner described for durability test A.

(3) Durability test C 1 gram of the highly absorbent resin is placed in a 500-ml Erlenmeyer flask equipped with a reflex condenser, 200 g of water is added, and the mixture is heated to 100° C. Boiling is continued for 48 hours, and the condition of the hydrous gel is observed. The result is reported in the manner described for durability test A.

(4) Heat resistance test D

The highly absorbent resin is heated at 150° C. for 8 hours. Thereafter, the absorbency (absorbing capacity) of the resin is measured for distilled water.

(5) Heat resistance test E

The highly absorbent resin is heated at 180° C. for 8 hours. Thereafter, the absorbency of the resin is measured for distilled water.

The results of these tests are shown in Table 1. As is evident from Table 1, the highly absorbent resin obtained in this example showed very excellent physical properties, namely good durability and good heat resistance.

EXAMPLES 2 AND 3

A mixture of 100 weight parts of isobutylene-maleic anhydride copolymer (the intrinsic viscosity [η] as measured in dimethylformamide at 30° C. being 0.62; the molar ratio of isobutylene to maleic anhydride in the copolymer being 1:1), 42 weight parts of potassium hydroxide (85% purity), 9 weight parts of 25% aqueous ammonia and 249 weight parts of water was stirred with heating to give a homogeneous aqueous solution of potassium ammonium neutralization product of the isobutylene-maleic anhydride copolymer. The degree of neutralization of said neutralization product was 0.6 (0.5 based on potassium hydroxide, 0.1 based on ammonia, 0.6 in total). To 400 weight parts of this aqueous solution was added 0.4 or 1 weight part of polyethyleneimine having a molecular weight of 600. After sufficient stirring, following the procedure of Example 1, each solution was formed into a film and the film was dried, heat-treated and crushed to give a highly absorbent resin powder.

The highly absorbent resins thus produced absorbed 360 and 140 g/g of distilled water, respectively. These resins were subjected to the durability tests described in Example 1, and the results as shown in Table 1 were obtained. As is evident therefrom, the highly absorbent resins were excellent in durability and heat resistance.

COMPARATIVE EXAMPLE 1

A highly absorbent resin containing potassium neutralization product of carboxyl groups and carboxy amide groups was prepared by graft copolymerizing acrylonitrile on starch, followed by hydrolysis with potassium hydroxide. The absorbency of this highly absorbent resin was 380 g/g. This highly absorbent resin was subjected to the durability tests as described in Example 1, and the results as shown in Table 1 were obtained.

TABLE 1

| Example No. | | 1 | 2 | 3 | |
|---|---|---|---|---|---|
| Comparative Example No. | | | | | 1 |
| Absorbency of highly absorbent resin (g/g of distilled water) | | 280 | 360 | 140 | 380 |
| Durability test[1] A | Room temperature, one year | O | O | O | X[2] |
| Durability test[1] B | 70° C., 30 days | O | O | O | Δ ~ X |
| Durability test[1] C | 100° C., 48 hours | O | O | O | X |
| Heat resistance test D | 150° C., 8 hours | 275 | 360 | 140 | <50[3] |
| (Absorbency, g/g) E | 180° C., 8 hours | 270 | 345 | 140 | <20[3] |

Notes:
[1]O: No change in the state of hydrous gel as compared with the initial state.
X: Partial dissolution of the hydrous gel.
Δ: Dissolution; the state of hydrous gel not retained.
[2]Putrefaction noted.
[3]Exact measurement was impossible due to partial dissolution of the highly absorbent resin.

EXAMPLE 4

A homogeneous aqueous solution was prepared by blending 100 weight parts of isobutylene-maleic anhydride copolymer as used in Example 1, 31 weight parts of sodium hydroxide and 369 weight parts of water. The degree of neutralization was 0.6. Polyethyleneimine having a molecular weight of 1,200 was added in various amounts as given in Table 2 to 500 weight parts of said aqueous solution. After sufficient stirring, each solution was poured into a square Teflon vat (70×70 cm). The film thus prepared was dried in air oven maintained at 120° C., then further heat-treated at 170° C. for 3 hours, and crushed to give a highly absorbent 20-mesh resin powder.

The thus-prepared highly absorbent resin was subjected to a test for absorbency for water (distilled water) and the durability tests as described in Example 1, and the results as shown in Table 2 were obtained.

TABLE 2

| Amount of poly-ethyleneimine* | Absorbency (g/g) | Durability test | | |
|---|---|---|---|---|
| | | A | B | C |
| 0.05 | — | O | O ~ X | X |
| 0.09 | ca. 1,500 | O | O ~ Δ | Δ |
| 0.14 | ca. 800 | O | O | O ~ Δ |
| 0.2 | 500 | O | O | O |
| 0.4 | 180 | O | O | O |
| 0.6 | 89 | O | O | O |
| 0.8 | 60 | O | O | O |
| 0.9 | 50 | O | O | O |
| 1.0 | 43 | O | O | O |
| 1.25 | 32 | O | O | O |
| 1.5 | 24 | O | O | O |
| 1.7 | 20 | O | O | O |
| 2.0 | 17 | O | O | O |
| 5.0 | 7 | O | O | O |

*Weight part(s) per 100 weight parts of the neutralization product (degree of neutralization: 0.6) prepared by treatment of isobutylene-maleic anhydride copolymer with sodium hydroxide.

The results given in the above table indicate that highly absorbent resins showing absorbency values of 20-800 g/g and having good durability can be obtained when polyethyleneimine is used in amounts of 0.14 to 1.7 weight parts.

Plotting the absorbency values against the amounts of polyethyleneimine on a logarithmic graph paper revealed a substantially straight line relationship therebetween. The gradient and section are determined by the kind of the carboxyl-containing polymer used, the degree of neutralization thereof, the kind and amount of the polyamine used. When epoxy compounds, polyhydric alcohols, aminoalcohols or isocyanates are used as the crosslinking agents, such a relationship can never be found. The relationship is specific to polyamines and makes it possible to obtain a highly absorbent resin with a desired absorbency directly.

EXAMPLE 5

By mixing 200 weight parts of isobutylene-maleic anhydride copolymer as used in Example 1 with 800 weight parts each of aqueous solutions containing various amounts of sodium hydroxide, there were prepared sodium neutralization product of isobutylene-maleic anhydride copolymer with various degrees of neutralization ($\alpha$) as given in Table 3. Then, 0.9 weight part of polyethyleneimine having a molecular weight of 300 was added to 1,000 weight parts of each aqueous solution, and the mixture was stirred. When sodium hydroxide was used in an amount of 36.4 weight parts, the viscosity of the system rapidly increased upon addition of polyethyleneimine, whereby stirring became difficult. A hot plate was coated with the aqueous solution, whereby drying was effected. The film so obtained was crushed, and the powder was subjected to heat treatment at 175° C. for 2 hours. Highly absorbent resins (A) to (H) showing absorbency values as shown in Table 3 were obtained.

TABLE 3

| Resin No. | Amount of sodium hydroxide | Degree of neutralization ($\alpha$) of isobutylene-maleic anhydride copolymer | Absorbency (g/g) of highly absorbent resin |
|---|---|---|---|
| A | 36.4 | 0.35 | 178 |
| B | 41.6 | 0.40 | 160 |
| C | 46.7 | 0.45 | 157 |
| D | 51.9 | 0.50 | 144 |
| E | 57.1 | 0.55 | 147 |
| F | 62.3 | 0.60 | 153 |
| G | 83.1 | 0.80 | 181 |
| H | 88.3 | 0.85 | 205 |

These highly absorbent resins were subjected to durability tests A, B and C as described in Example 1, and the results as shown in Table 4 were obtained.

TABLE 4

| Resin No. | Degrees of neutralization ($\alpha$) | Durability test A (room temp., one year) | B (70° C., 30 days) | C (100° C., 48 hours) |
|---|---|---|---|---|
| A | 0.35 | Δ | X | X |
| B | 0.40 | O | X | X |
| C | 0.45 | O | Δ | X |
| D | 0.50 | O | O | O |
| E | 0.55 | O | O | O |
| F | 0.60 | O | O | O |
| G | 0.80 | O | O | O |
| H | 0.85 | Δ~X | X~Δ | X~Δ |

O: No change in the state of hydrous gel as compared with the initial state.
X: Partial dissolution of the hydrous gel.
Δ: Dissolution; the state of hydrous gel not retained.

EXAMPLE 6

A homogeneous aqueous solution of sodium neutralization product of styrene-maleic anhydride copolymer was prepared by mixing and heating 100 weight parts of styrene-maleic anhydride copolymer (the intrinsic viscosity [$\eta$] as measured in dimethylformamide at 30° C. being 1.85; the molar ratio of styrene to maleic anhydride in the copolymer being 1:1; in Table 5, referred to as St-Man), 28 weight parts of sodium hydroxide and 372 weight parts of water. The degree of neutralization of the neutralization product was 0.7. To 500 weight parts of this aqueous solution was added 0.5 weight part of tetraethylenepentamine. After adequate stirring, the solution was applied to a hot roll with a surface temperature of 125° C. The thus-formed and dried film was crushed to form a 20 mesh powder, which was heat-treated at 140° C. for 16 hours to give a highly absorbent resin powder.

The thus-obtained highly absorbent resin (powder) was tested for absorbency with water (distilled water), 5% sodium chloride solution, 5% aqueous sodium hydroxide solution, Ringer solution and artificial urine, and also subjected to the heat resistance tests described in Example 1. The results of these tests were as shown in Table 5.

As is evident from the data in Table 5, this highly absorbent resin (tetraethylenepentamine-crosslinked sodium neutralization product of styrene-maleic anhydride copolymer) was excellent in absorbency for a variety of liquids as well as in heat resistance, wherein as absorbent resin consisting of tetraethylenepentamine-crosslinked ammonium neutralization product of styrene-maleic anhydride copolymer, as mentioned hereinbelow, was largely effected in absorbency thereof by the presence of salts in aqueous liquids, to which it responded with much decreased absorbency values, and was almost completely deprived of its water-absorbing capacity upon heating at 150° C. or 180° C.

COMPARATIVE EXAMPLE 2

A highly absorbent resin was prepared by repeating the procedure of Example 6 using 53 weight parts of 25% aqueous ammonia and 347 weight parts of water instead of 28 weight parts of sodium hydroxide and 372 weight parts of water.

The highly absorbent resin obtained was subjected to the same tests as in Example 6, and the results as shown in Table 5 were obtained.

TABLE 5

| Highly absorbent resin | | Example 6 Tetraethylene-pentamine-cross-linked sodium neutralization product of St-MAn | Comparative Example 2 Tetraethylene-pentamine-cross-linked ammonium neutralization product of St-MAn |
|---|---|---|---|
| Absorbency (g/g) for | Distilled water | 185 | 180 |
| | Aqueous NaCl solution | 63 | 30 |
| | Aqueous NaOH solution | 68 | 31 |
| | Ringer solution | 50 | 23 |
| | Artificial urine | 39 | 16 |
| Heat resistance test D (150° C., 8 hours) | | 171 | 0.6 |
| Heat resistance test E (180° C., 8 hours) | | 168 | 0.4 |

St-MAn: Styrene-maleic anhydride copolymer

EXAMPLE 7

An aqueous solution of sodium polyacrylate with a degree of neutralization of 0.75 was prepared by adding 42 weight parts of sodium hydroxide to 500 weight parts of an aqueous polyacrylic acid solution (20% solution; the viscosity of the solution at 25° C. being 250 centipoises). To this solution was added 0.35 weight part of polyethyleneimine having a molecular weight of 600. After sufficient stirring, the solution was poured into a square Teflon vat (70×70 cm). The film thus formed was dried in an air oven maintained at 120° C., further heat-treated at 160° C. for 3 hours, and then crushed to form a highly absorbent 20-mesh resin powder.

The absorbency of this highly absorbent resin was 155 g/g of distilled water. A hydrous gel was prepared by adding 150 weight parts of water to 1 weight part of the resin. The hydrous gel was placed in an air oven maintained at 80° C. and water was allowed to evaporate ("evaporation"), and, when the amount of water reduced to 50 weight parts, heating was discontinued and 100 weight parts of water was added ("water feeding"). After said evaporation-water feeding process was repeated ten times in all, the condition of the hydrous gel was quite the same as the initial one, and no substantial change in water-absorbing capacity was noted.

Furthermore, when 1 weight part of this highly absorbent resin was added to 200 weight parts each of 0.5 N aqueous sodium hydroxide and 0.5 N sulfuric acid and the mixtures were heated at 80° C. for a fairly long period of time, the highly absorbent resin was not dissolved but retained a constant gel strength.

Having now fully described this invention, it will be apparent to one or ordinary skill in the art that many changes and modifications can be made thereto without departing from the spirit or scope of the invention set forth herein.

What is claimed as new and desired to be secured by Letters Patent of the United States is:

1. A highly absorbent resin which is essentially a polyamine-crosslinked, partial neutralization product obtained by reaction of an alkali metal hydroxide with a carboxyl-containing polymer selected from the group consisting of alpha-olefin-maleic anhydride copolymers, vinyl compound-maleic anhydride copolymers, polyacrylic acid, polymethacrylic acid, and mixtures thereof, the degree of neutralization of said neutralization product being within the range of 0.4 to 0.8 equivalent of total carboxyl groups of the said carboxyl-containing polymer, the amount of polyamine having a general formula shown by $H-(NH-CH_2CH_2)_n NH_2$, wherein n is an integer of 1 to 110, as a crosslinking agent, being not more than 2 parts by weight per 100 parts by weight of the neutralization product on the uncrosslinked basis, said resin being capable of absorbing at least 20 times its own weight of distilled water.

2. The highly absorbent resin of claim 1, wherein the carboxyl-containing polymer is an alpha-olefin-maleic anhydride copolymer.

3. The highly absorbent resin of claim 2, wherein the alpha-olefin is isobutylene.

4. The highly absorbent resin of claim 1, wherein the carboxyl-containing polymer is a vinyl compound-maleic anhydride copolymer.

5. The highly absorbent resin of claim 4, wherein the vinyl compound is styrene.

6. The highly absorbent resin of claim 1, wherein the carboxyl-containing polymer is a polyacrylic acid.

7. The highly absorbent resin of claim 1, wherein the alkali metal hydroxide is sodium hydroxide.

8. The highly absorbent resin of claim 1, wherein the degree of neutralization of said partial neutralization product is 0.5 to 0.8.

9. The highly absorbent resin of claim 1, wherein the polyamine is polyethyleneimine.

10. The highly absorbent resin of claim 1, wherein the polyamine is a water-soluble polyamine selected from the group consisting of ethylenediamine, diethylenetriamine, triethylenetetramine, tetraethylenepentamine and pentaethylenehexamine.

11. The highly absorbent resin of claim 1, wherein the amount of polyamine is 0.14 to 1.7 parts by weight per 100 parts by weight of the alkali metal neutralization product of carboxyl-containing polymer on the uncrosslinked basis.

12. The highly absorbent resin of claim 1, which is a polyethyleneimine-crosslinked, partial sodium neutralization of isobutylene-maleic anhydride copolymer, the degree of neutralization of the neutralization product being 0.5 to 0.8 equivalent of total carboxyl groups of the said copolymer, the amount of polyethyleneimine being 0.14 to 1.7 parts by weight per 100 parts by weight of the neutralizate on the uncrosslinked basis, said resin being capable of absorbing 20 to 800 times its own weight of distilled water.

13. The highly absorbent resin of claim 1, wherein the carboxyl-containing polymer is selected from the group consisting of copolymers of one mole of an alpha-olefin containing 2–12 carbon atoms and about one mole of maleic anhydride; copolymers consisting of one mole of a vinyl compound selected from the group consisting of styrene, vinyl chloride, vinyl acetate, vinyl propionate, acrylonitrile, methyl vinyl ether, and acrylic acid esters and about one mole of maleic anhydride; polyacrylic acid; polymethacrylic acid; and mixtures thereof.

14. The highly absorbent resin of claim 13, wherein said alpha-olefin is an alpha-olefin containing 2–12 carbon atoms.

15. The highly absorbent resin of claim 14, wherein said alpha-olefin contains 2–8 carbon atoms.

* * * * *